United States Patent [19]

Damadian

[11] Patent Number: 5,606,970
[45] Date of Patent: Mar. 4, 1997

[54] MULTIPLE PATIENT SCANNING ON A MAGNETIC RESONANCE IMAGING APPARATUS

[75] Inventor: Raymond V. Damadian, Woodbury, N.Y.

[73] Assignee: Fonar Corporation, Melville, N.Y.

[21] Appl. No.: 952,327

[22] Filed: Sep. 28, 1992

[51] Int. Cl.⁶ .................................................. A61B 5/055
[52] U.S. Cl. ...................... 128/653.2; 324/309; 324/318
[58] Field of Search .............................. 128/653.2, 653.5; 324/309, 318; 5/601; 378/20, 68, 208, 209

[56] References Cited

U.S. PATENT DOCUMENTS

| | | | |
|---|---|---|---|
| 4,668,915 | 5/1987 | Daubin et al. | 324/309 |
| 4,770,182 | 9/1988 | Damadian et al. | 128/653.2 |
| 4,771,785 | 9/1988 | Duer | 324/318 |
| 4,805,626 | 2/1989 | DiMassimo et al. | 128/653.5 |
| 4,829,252 | 5/1989 | Kaufman | 324/318 |
| 4,885,540 | 12/1989 | Snoddy et al. | 324/318 |
| 5,197,474 | 3/1993 | Englund et al. | 128/653.5 |
| 5,204,629 | 4/1993 | Ueyama | 128/653.5 |

Primary Examiner—Ruth S. Smith
Assistant Examiner—Brian L. Casler
Attorney, Agent, or Firm—Brooks Haidt Haffner & Delahunty

[57] ABSTRACT

Magnetic resonance imaging systems typically have a single patient handling system which allows the sequential scanning of individual patients. Such apparatus limit patient throughput and consequently the utility of magnetic resonance imaging systems. The present invention details apparatus and methods to enhance patient throughput of a magnetic resonance imaging system. Two distinct components of a magnetic resonance imaging procedure are defined: the patient handling time and the scan protocol time, and these time components are multiplexed to enhance patient throughput. This is achieved by addition of patient handling systems at additional apertures as exist on the primary field magnet and which provide access to the imaging volume. It is thus possible, for example, to have the patient handling time component of one patient overlap with the scan protocol time component of a second patient. Additionally, the presence of more than one patient handling system permits the simultaneous image data acquisition on more than one patient.

55 Claims, 4 Drawing Sheets

MULTIPLE PATIENT SCANNING ON A MAGNETIC RESONANCE IMAGING APPARATUS

BACKGROUND OF THE INVENTION

The present invention pertains to medical nuclear magnetic resonance scanners, particularly as employed during magnetic resonance imaging (MRI) procedures.

Since the invention of the medical nuclear magnetic resonance (NMR) scanning technique by Dr. Raymond Damadian, as set forth in U.S. Pat. No. 3,789,832, this technique has been widely adopted in the medical arts. Medical NMR scanning requires creation of a substantial constant "primary" magnetic field passing through the patient's body. Additional "gradient" magnetic fields varying with time typically are superimposed on the primary field. The patient is exposed to radio frequency electromagnetic waves which also vary with time in particular patterns. Under the influence of the magnetic fields and the radio waves, certain atomic nuclei within the patient's tissues resonate and emit further radio waves. By known mathematical techniques involving correlation of the magnetic field patterns in use at various times with the radio frequency waves emitted, it is possible to determine physical condition at various locations within the patient's body. This information typically is displayed as an image with intensity corresponding to the concentration and/or physical state of certain nuclei of interest. The concentrations or physical state of different substances ordinarily differ for differing kinds of tissues within the body, and also permits the physician to see abnormalities, such as tumors, within the body. Accordingly, MR imaging techniques have been widely adopted by physicians.

Present day magnetic resonance scanners typically possess a patient handling system which is in close proximity to an aperture of the magnet responsible for generating the primary magnetic field. The patient handling system is used to position the anatomical region of interest to be investigated during an MRI procedure, into a portion of the primary magnetic field referred to as the imaging volume.

Following the completion of the scan protocol, the patient is removed from the magnet and unloaded from the patient handling system, and preparations for the next patient are made. Such a series of events is repeated for each patient to be subjected to an MRI procedure.

Magnetic resonance imaging practiced in such a way limits the utilization of the magnetic resonance scanner since only one patient at a time is submitted to a magnetic resonance imaging procedure. Such practices contribute to the high cost of medical care and slow the dissemination of this valuable diagnostic tool.

It is the objective of this invention to described approaches which improve the utilization of magnetic resonance scanners by multiplexing patient processing in order to enhance patient throughput.

SUMMARY OF THE INVENTION

The present invention comprises methods and apparatus which will provide enhanced patient throughput on medical magnetic resonance scanners.

The present invention provides for access to the imaging volume of the primary magnetic field through additional apertures as exist in the magnet structure. Magnetic resonance scanners in use today make use of one of the three types of magnets: superconducting, resistive and permanent. Virtually every magnet in present use has two available apertures capable of providing access to the imaging volume. The present invention makes use of both apertures by means of a separate patient handling system at each aperture, each of which permits placement of a patient to be subjected to a magnetic resonance imaging procedure in the imaging volume.

The time required for a magnetic resonance imaging procedure has two major components. The first component is related to conducting a scan protocol which is the time required to collect the spatially encoded magnetic resonance imaging data. Imaging data will subsequently be processed into magnetic resonance images. The scan protocol time accounts for anywhere from 30% to 70% of the total imaging procedure time, depending upon the precise nature of the scan protocol being used. The second major component of the MR imaging procedure, which accounts for the remainder of the total time, is the patient handling time. Patient handling time is comprised of preparation of the patient, loading the patient onto the patient handling system, placing the patient through the magnet aperture into the imaging volume, positioning the radio frequency coils onto or about the patient, attaching any ancillary equipment necessary for a particular patient or scan protocol, removing the patient following completion of the scan protocol, unloading the patient from the patient handling system, and preparing the scanner for the next patient.

The present invention addresses the need to reduce the amount of time spent on each of the two major time components of the magnetic resonance scanning procedure.

In one embodiment of the present invention, multiple patient handling systems permit patient handling of a patient, in preparation for positioning in the imaging volume while the scan protocol of another magnetic resonance imaging procedure is being conducted on a different patient. The different patient had been positioned previously in the imaging volume on a separate patient handling system. This procedure permits the time overlapping of the two major time components of separate magnetic resonance imaging procedures.

In another embodiment of the present invention, two patients to be subjected to a magnetic resonance imaging procedure may be positioned in the imaging volume simultaneously, where each one is afforded access to the imaging volume through a separate aperture by means of a separate patient handling system. Following this, a single scan protocol, which is comprised of multiple scans, may be conducted, resulting in simultaneous magnetic resonance imaging data acquisition for both patients. Such a procedure results in a substantial reduction of the scan protocol time component of the magnetic resonance imaging procedure, and increased patient throughput.

For conceptual simplicity, the present invention has been described in terms of two patients, and two patient handling systems with each one providing access to an imaging volume through a separate and distinct aperture of the primary magnet. It will be appreciated that a scanner with a multiple aperture primary magnet, and multiple patient handling systems capable of scanning a multiplicity of patients, is desirable and within the scope of the present invention.

Thus, another embodiment of the present invention includes a multiplicity of patient handling systems each of which is capable of positioning a patient, or more specifically the anatomical region of interest thereof, into the imaging volume of the primary magnetic field. Additional throughput enhancement will result as more magnet apertures are utilized and the degree of enhancement will be generally proportional to the number of patient handling systems employed up to a limit where the imaging volume is not large enough to accommodate additional patients.

DETAILED DESCRIPTION OF THE PREFERRED EMBODIMENTS

A nuclear magnetic resonance scanner generally is comprised of several major subsystems including the primary field magnet, gradient magnetic field subsystem, nuclear magnetic resonance spectrometer, image processing and display subsystem, patient handling subsystem, and radio frequency subsystem. The present invention is concerned with the primary field magnet, the radio frequency subsystem, and the patient handling subsystem, and generally relates to scanning apparatuses and methods which employ a multiplicity of patient handling systems, each one capable of positioning a patient in the imaging volume in preparation for a magnetic resonance scan protocol. The scan protocol of a magnetic resonance imaging procedure is carried out on individual patients or on more than one patient simultaneously. For the purposes of this discussion, the gradient magnetic field subsystem is correctly and permanently situated with respect to the primary magnetic field magnet and thus positioning a patient in the imaging volume of the primary field magnet will automatically position the patient with respect to the gradient magnetic field as well.

As shown in a lateral view (FIG. 1), a magnetic resonance scanner having a magnet 1 for generating the primary magnetic field contains two apertures 2 which are opposed to each other. The apertures 2 provide access to an imaging volume 3, where the requisite primary and gradient magnetic fields necessary to conduct a magnetic resonance scan protocol are generated. Also included in the imaging volume 3 are the radio frequency antennas 4 which will be used to stimulate, and receive signals from, the nuclei participating in the nuclear magnetic resonance response.

Figure 1:
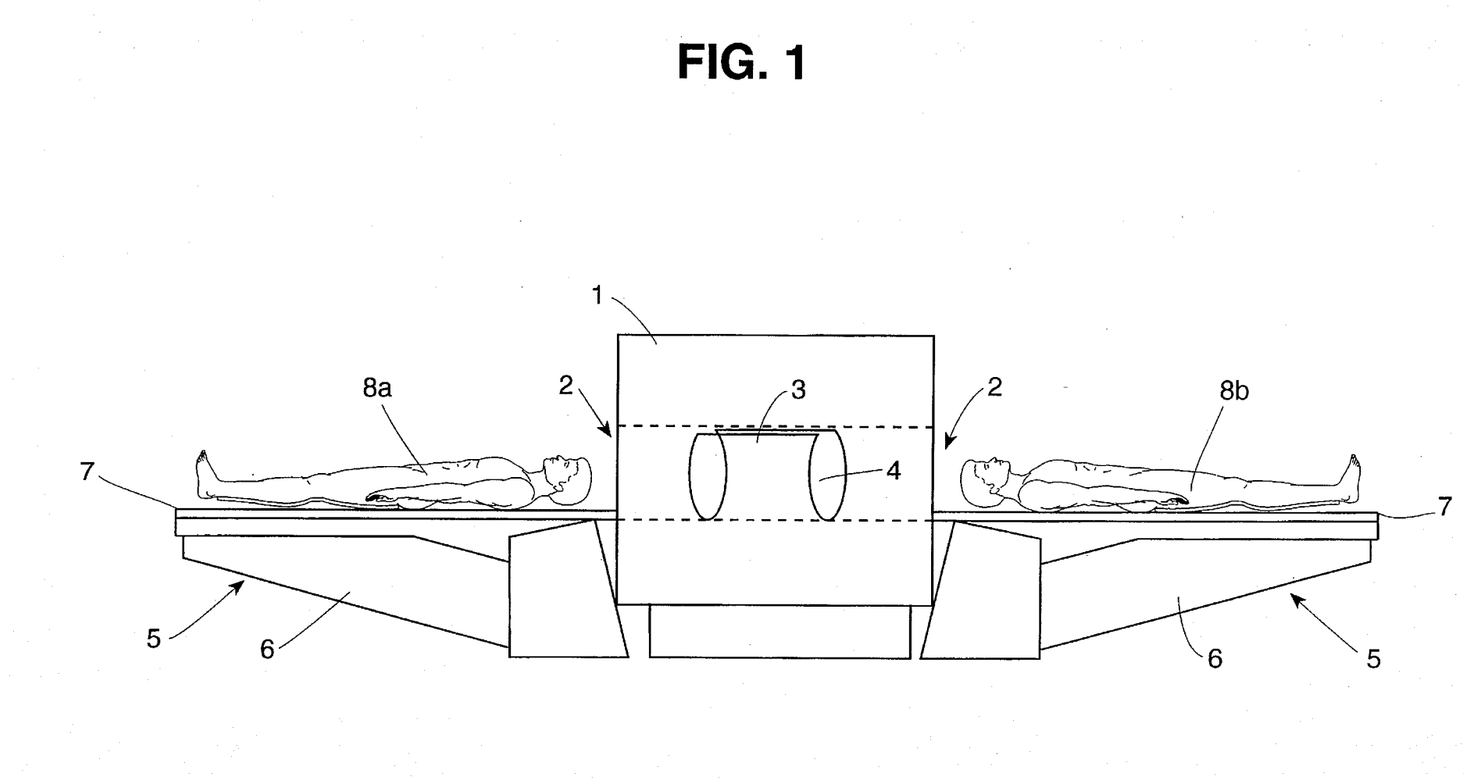
FIG. 1: Lateral View showing a patient handling system at each of two apertures of a primary field magnet.

FIG. 1 also shows two patient handling systems 5, where each one is positioned to provide access to the imaging volume through one of the two opposed apertures 2 in the primary magnet 1. Each patient handling system is comprised of a base support structure 6 and a movable bed structure 7 upon which the patient lies. The movable bed structure 7 provides a means for moving the patient from outside the primary magnet 1, into and out of the imaging volume 3, and also provides a means for the precise positioning of the anatomical region of interest of the patient (8a, 8b) in the imaging volume 3.

Figure 2:
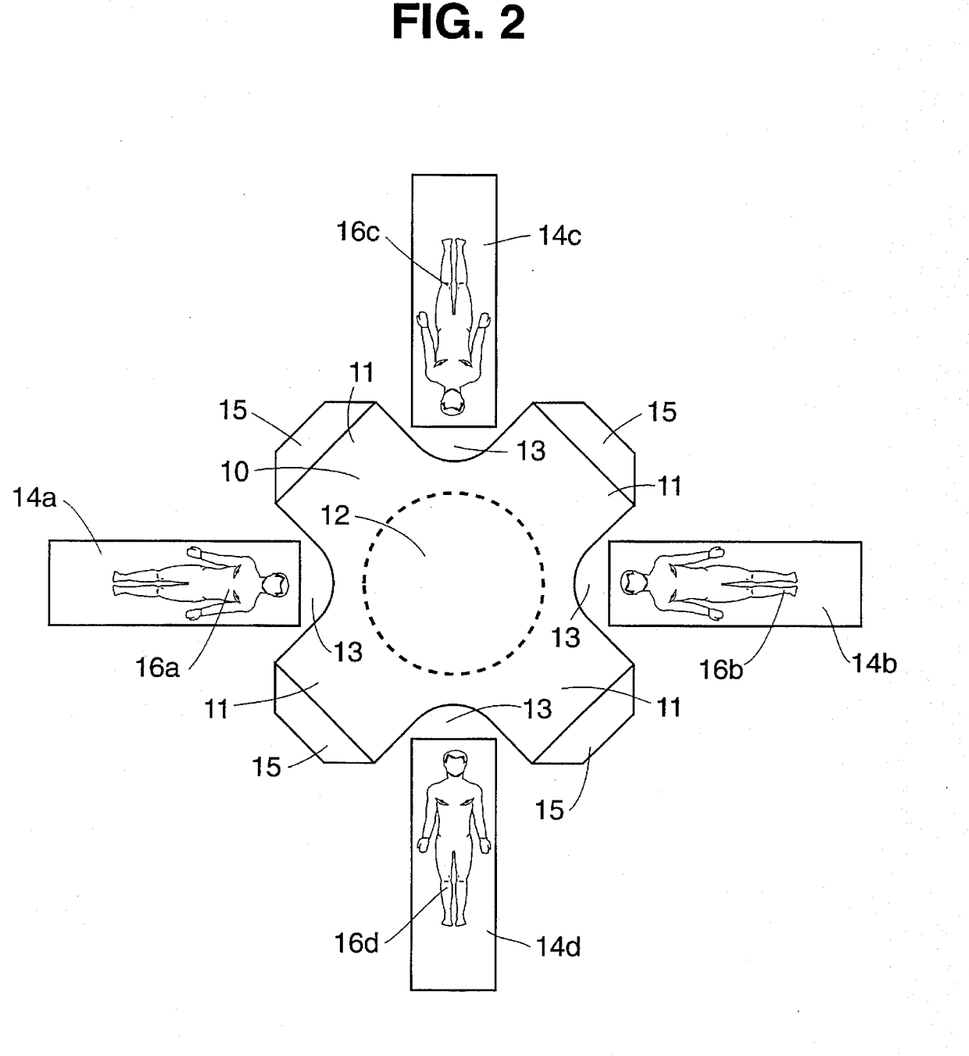
FIG. 2: A plan view of a primary field magnet having four apertures with a patient handling system proximate each aperture.

A second embodiment of the present invention is illustrated in FIG. 2. The top plate 10 of an iron core magnet is connected to a bottom plate (not shown) of the same size, shape and orientation by a set of four vertical support columns 15, each one of which connects at one of the four protrusions 11 of the top plate of the magnet structure and a corresponding protrusion on the bottom plate of the magnet structure (not shown). The top plate 10 and bottom plate of the magnet are aligned such that the interconnecting support columns are vertical, and parallel with each other.

Such a magnet structure will contain an imaging volume 12 with access provided through as many as four apertures 13 one each between adjacent vertical columns of steel which join the top and bottom horizontal plates of the magnet. Each aperture is accessed with a patient handling system (14a, 14b, 14c, 14d), thus providing the capability of processing as many as four patients simultaneously. This results in greatly enhancing the throughput of the magnetic resonance scanner.

The apparatuses which are described in FIG. 1 and FIG. 2 of the present invention may be employed to practice other embodiments of the present invention, as related to conducting magnetic resonance imaging procedures.

One example of this, based on FIG. 1, is a method which comprises subjecting one patient (for example 8a) to the scan protocol time component of a magnetic resonance imaging procedure after positioning the patient in the imaging volume, and simultaneously preparing the second patient 8b, for the scan protocol time component of a second magnetic resonance imaging procedure. This overlapping of scan protocol and patient handling functions using two patient handling systems results in a significant enhancement of scanner utilization.

Another method of the present invention is illustrated using the apparatus shown in FIG. 1. Here, each of two patients (8a, 8b), laying on their respective movable bed structure 7 of the patient handling systems 5, is translated through the aperture and positioned in the imaging volume in such a manner as necessary to perform an MR scan protocol of the head region of both patients simultaneously. In general, proper positioning involves placing the anatomical region of interest of each patient at a particular location in the primary magnetic field imaging volume 3 and having the radio frequency antennas 4, positioned in close proximity to the patient's anatomical region of interest.

Radio frequency antenna systems used in magnetic resonance imaging exist as a combination of single mode antennas, in which case each antenna will serve either as a transmitter or receiver of radio frequency energy. Alternatively, antennas may be designed to function in both a transit and receive mode, consequently requiring only a single antenna to conduct an MR scan protocol. Implementation of the radio frequency antennas, whether operated in single mode as an antenna system or dual mode may occur by having the antenna(s) in a fixed location in the imaging volume. In this instance, a patient is moved into the imaging volume 3 by means of the movable bed structure 7 and proper positioning is achieved simply by positioning the patient such that the anatomical region of interest which is the subject of the MR imaging procedure occupies a place in the imaging volume which has the requisite magnetic field uniformity and radio frequency antenna radiation patterns. Alternatively, the transmitter coil, receiver coil, or dual mode transmitter/receiver coil may be positioned relative to the anatomical region of interest of the patient prior to movement of the patient into the imaging volume 3 by the movable bed structure 7.

Positioned inside the primary magnet and proximate the imaging volume 3 are the radio frequency antennas 4 whose radiation pattern extends over a portion of the imaging volume large enough to cover the head region of two patients (8a, 8b). The head region of each patient is positioned in opposite ends of the receiver coil structure, at which point the MR scan protocol may proceed.

It should be appreciated that the same method may be practiced on an apparatus with more than two patient handling systems. Thus, still another embodiment of this invention involves four patients (FIG. 2) where each patient (16a, 16b, 16c, 16d) is laying on one of the four patient handling systems 14a, 14b, 14c, 14d respectively, each of which provides access to the imaging volume 12. Two of the patients (16a, 16b) are moved into the imaging volume 12, in the process properly positioning the anatomical region of interest of each patient with respect to the primary magnetic field, and the radio frequency antennas. At this point, an MR scan protocol may commence. As the acquisition of MR imaging data proceeds, preparation of an alternate pair of patients (16c, 16d) for a subsequent scan protocol with each one laying on one of the two remaining patient handling systems, may proceed. At such time as the imaging procedure on the first pair of patients is completed, they may be removed from the imaging volume, followed by placement of the alternate pair of patients (16c, 16d) into the imaging volume to conduct another scan protocol. The procedure of sequential scanning and preparation of alternate pairs of patients is repeated. Alternatively, the apparatus in FIG. 2 may be used to scan patients individually rather than in pairs.

The simultaneous scanning of more than one patient has been described for purposes of illustration in terms of opposed patients on a magnetic resonance scanning system having a magnet with four apertures, and with each aperture being accessed by a patient handling system. This embodiment is not meant to be restricted to the use of opposed patients. Thus, adjacent patients may also be scanned simultaneously. Generalizing this to a system containing a multiplicity of apertures and a multiplicity of patient handling systems, simultaneous scan protocols performed on any number of patients, regardless of their spatial relationships with respect to their position in the imaging volume, is considered to be within the scope of the present invention.

The scan protocol which is part of the magnetic resonance imaging procedure is generally comprised of a pulse sequence designed to yield spatially encoded imaging data, which, when appropriately processed, yields diagnostically important information. In methods involving acquisition of such imaging data from an individual patient, the scan protocol typically involves executing a single pulse sequence, or series of pulse sequences. In the methods according to the present invention involving acquisition of such imaging data from two or more patients simultaneously, a scan protocol can acquire imaging data from a pulse sequence or series of pulse sequences as follows: (a) in queue mode, from each patient successively; (b) in interleaved mode, where each portion of the entire data acquisition contains imaging data from only one of multiple patients, and where the separate portions of the entire data acquisition are collected in interleaved fashion; (c) in multipatient mode, where each portion of the entire data acquisition contains imaging data from more than one patient; (d) or in any combination of queue mode, interleaved mode and multipatient mode of data acquisition.

In the case of multipatient mode scanning of more than one patient, where magnetic resonance imaging data from more than one patient would be contained in individual images, it is necessary to provide means for separation of image data such that data collected for each patient may be diagnosed and archived separately.

Figure 3:
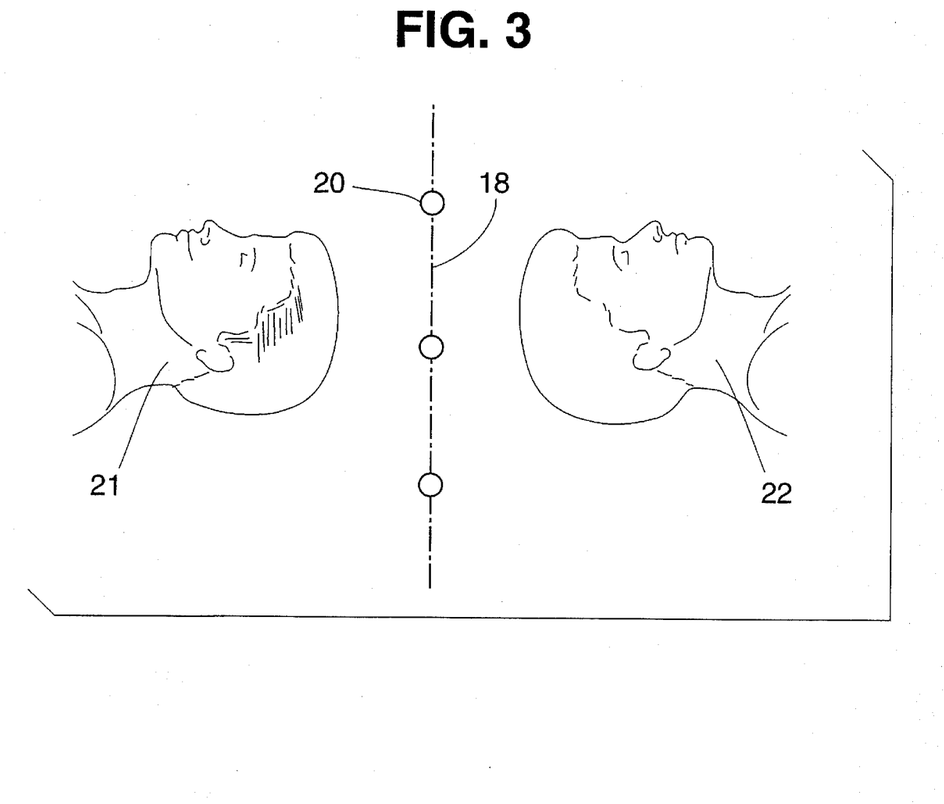
FIG. 3: The field of view of a sagittal image obtained during simultaneous magnetic resonance imaging procedures on two patients, along with fiducial markers.

In FIG. 3 fiducial markers 20 are small amounts of material which are capable of generating a magnetic resonance signal, and which, when placed in known positions in the imaging volume of the primary magnetic field, serve to mark a specific location in the field of view of an image, which is obtained during a magnetic resonance imaging procedure. As an example of how fiducial markers may be used, consider the case of a magnetic resonance scan protocol conducted in multipatient mode on the head regions of two patients where the scan protocol is performed using a sagittal orientation. The field of view of the resultant images will contain image data as shown in FIG. 3. These data are represented as two distinct and separable sagittal head images 21 and 22. Fiducial markers 20 appear in the field of view of the final image at fixed positions. Such positions are chosen to demarcate the effective boundaries in the imaging volume for each patient.

Figure 4A:
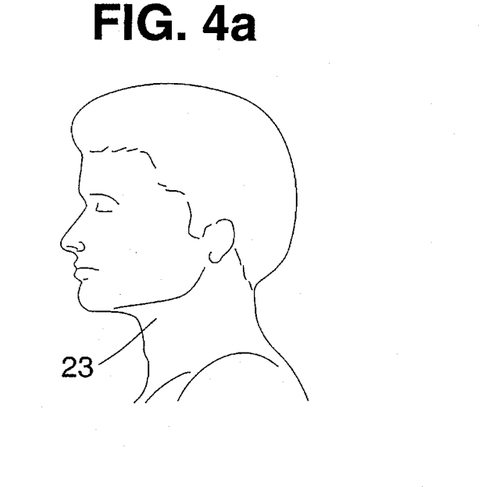
FIG. 4a, 4b: Individual images resulting from the separation and reorientation of image data obtained during simultaneous magnetic resonance imaging procedures on two patients.
Figure 4B:
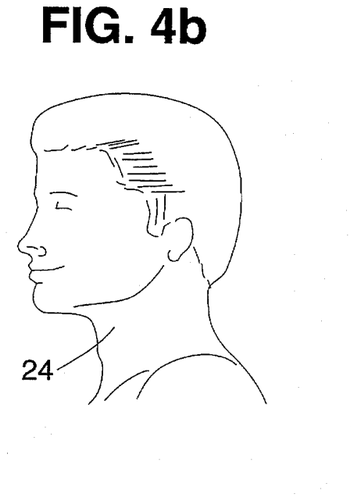

The NMR response of the fiducial markers may be used as a basis to separate the image data for the two patients. Processing of the image data therefore involves recognition of these fiducial markers on the basis of their NMR response, and the separation, and reorientation of the distinct data sets, consistent with the patient positioning during the acquisition of the data. Thus, the image data shown in FIG. 3 may be separated along a vertical demarcation line 18. The left data set is then rotated 90° counterclockwise; and the right data set is rotated clockwise 90°, and subsequently reversed with respect to left and right. The result of these operations is two separated images, 23 and 24 in FIG. 4a, and FIG. 4b, each from a different patient and represented in a standardized orientation for subsequent diagnosis. It should be apparent that, with the proper incorporation of fiducial markers into the scanning procedure, the process described for separation of images related to different patients may be generalized for any number of patients and yield scans with any desired orientation.

Alternative methods may also be used to separate the image data for multiple patients from a single image. These include using non-signal producing zones in the field of view of an image as a means of demarcation. Such methods are also within the scope of the present invention.

Figure 5:
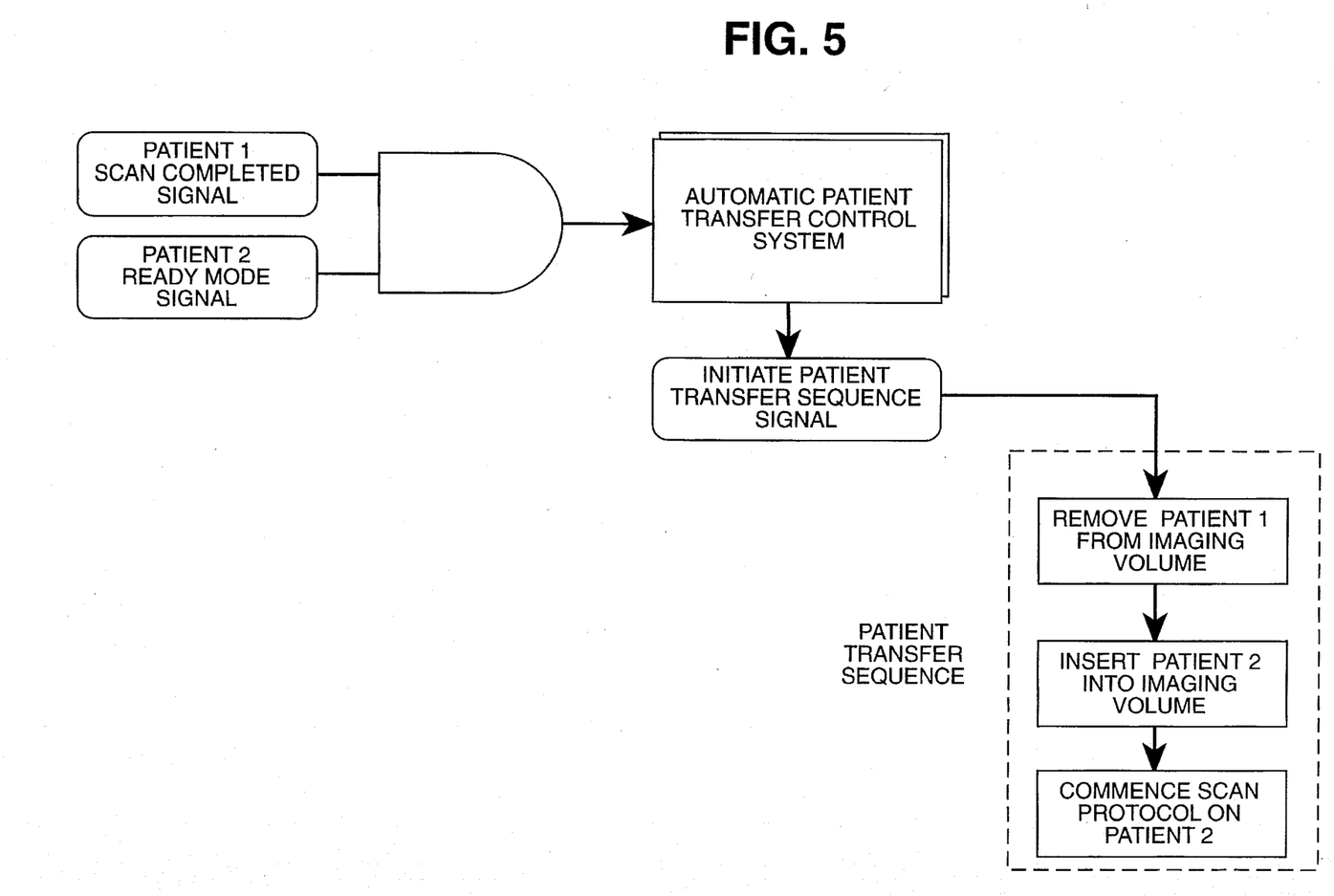
FIG. 5: Flow Chart showing an automatic patient transfer sequence.

In addition to the gains in patient throughput which result from implementation of the embodiments as already detailed, further improvement will be realized through automation of the switching from the patient handling component to the scan protocol component of the magnetic resonance imaging procedure. This is illustrated in FIG. 5, and is accomplished as follows: During the scan protocol on one patient, a second patient is prepared to undergo a scan protocol on a second patient handling system. When preparation is complete, the second patient will be ready to undergo a scan protocol, which cannot commence until the scan protocol on the first patient is completed. This ready state for the second patient is relayed electronically by the operator, who has prepared the second patient for the scan protocol, to an automatic patient transfer control system. The ready state signal will allow an automatic patient transfer sequence to follow completion of the scan protocol on the first patient. Such a sequence includes removal of the first patient from the imaging volume, placement of the second patient in the imaging volume, and initiation of the scan protocol on the second patient. This automatic patient transfer sequence is accomplished without scanner operator intervention, and is initiated by a logical AND, i.e., by the existence of two signals in the control system. One signal indicates that a patient not presently being subjected to a scan protocol is ready to be scanned, and the second signal indicates the scan protocol on the patient presently in the imaging volume has been completed. This second signal will be generated by the subsystem responsible for control of the scan protocol.

Execution of an automatic patient transfer sequence also requires activating the sequential movement of the patient bed structures by a signal from the automatic patient transfer control system. The placement of a patient in, and the removal of a patient from, the imaging volume is accomplished by activating and deactivating a motor which is attached to the patient bed structure of each patient handling system.

The automatic patient transfer control system is comprised of digitally programmable electronics which are part of the standard magnetic resonance scanning apparatus. Programming the control system will enable it to process input signals, generate control signals, and sequence events, all of which are required to execute an automatic patient transfer sequence.

The mode of operation involving an automatic patient transfer sequence may be practiced as related to the embodiment of this invention where single patients are being subjected to a scan protocol, as well as the embodiments involving simultaneous scanning of more than one patient. In the latter case, a ready mode signal and scan completed signal will be generated for more than one patient, and the sequential movement of the patient bed structures will be conducted on more than two beds.

I claim:

1. A medical magnet resonance imaging system comprising:
    (a) a magnet having a non-electromagnetically partitioned, common imaging volume for receiving anatomical regions of interest of multiple patients therein and having multiple apertures therethrough, each said aperture providing patient access to the common imaging volume;
    (b) multiple patient handling systems, each of said patient handling systems accessing said imaging volume through a respective one of said multiple apertures of said magnet, and each of said patient handling systems providing a means for positioning a respective one of said anatomical regions of interest of one of said multiple patients within said imaging volume of said magnet; and
    (c) a radio frequency antenna system for transmitting radio frequency energy into said imaging volume, and detecting magnetic resonance imaging data from each of said anatomical regions of interest for each of said patients within said imaging volume of said magnet.

2. The medical magnetic resonance imaging system as described in claim 1, wherein said magnet has two apertures.

3. The medical magnetic resonance imaging system as described in claim 1 having two patient handling systems.

4. The medical magnetic resonance imaging system as described in claim 1, wherein said radio frequency antenna system comprises a single radio frequency antenna that transmits radio frequency energy into said common imaging volume and receives radio frequency energy from the anatomical regions of each of said patients.

5. The medical magnetic resonance imaging system as described in claim 1, wherein said patient handling systems comprise motorized patient bed structures.

6. The medical magnetic resonance imaging system as described in claim 5, further comprising automatic patient sequence control means for automatically sequencing the patient handling systems to move the respective patient into and out of the imaging volume.

7. The medical magnetic resonance imaging system as described in claim 5, wherein said motorized patient bed structures are remotely controlled.

8. The medical magnetic resonance imaging system as described in claim 1, wherein each of said multiple apertures of said magnet has an axis along which said patient accesses the common imaging volume and at least two of said axes intersect.

9. The medical magnetic resonance imaging system as described in claim 1, wherein said imaging volume comprises at least one fiducial marker positioned to separate said anatomical regions of interest of said patients.

10. The medical magnetic resonance imaging system ad described in claim 1, wherein said imaging volume is dimensioned such that substantially less than each patient's entire body is received within the volume.

11. A medical magnetic resonance imaging system comprising:
    (a) a magnet having an imaging volume for receiving anatomical regions of interest of multiple patients therein and having multiple apertures therethrough, each said aperture providing patient access to the imaging volume;
    (b) multiple patient handling systems, each of said patient handling systems accessing said imaging volume through a respective one of said multiple apertures of said magnet, where at least two of said patient handling systems are in simultaneous use positioning anatomical regions of interest of at least two patients, respectively, within said imaging volume of said magnet; and
    (c) a radio frequency antenna system for detecting magnetic resonance imaging data simultaneously from the anatomical regions of interest of said at least two patients within said imaging volume.

12. The medical magnetic resonance imaging system as described in claim 11, wherein two of said patient handling systems simultaneously position anatomical regions of interest of two of said patients within said imaging volume of said magnet.

13. The medical magnetic resonance imaging system as described in claim 11, wherein said antenna system comprises a single radio frequency antenna that transmits radio frequency energy into said imaging volume and receives radio frequency energy from the anatomical regions of each of said patients.

14. The medical magnetic resonance imaging system as described in claim 11, wherein said patient handling systems comprise motorized patient bed structures.

15. The medical magnetic resonance imaging system as described in claim 14, further comprising automatic patient sequence control means for automatically sequencing the patient handling systems to move the respective patient into and out of the imaging volume.

16. The medical magnetic resonance imaging system as described in claim 14, wherein said motorized patient bed structures are remotely controlled.

17. The medical magnetic resonance imaging system as described in claim 11, wherein each of said multiple apertures of said magnet has an axis along which said patient accesses the common imaging volume and at least two of said axes intersect.

18. The medical magnetic resonance imaging system as described in claim 11, wherein said imaging volume comprises at least one fiducial marker to separate said anatomical regions of interest of said patients.

19. The medical magnetic resonance imaging system as described in claim 11, wherein said imaging volume is non-electromagnetically partitioned.

20. The medical magnetic resonance imaging system as described in claim 11, wherein said imaging volume is dimensioned such that substantially less than each patient's entire body is received within the volume.

21. A medical magnetic resonance imaging system comprising:
(a) a magnet having an imaging volume for receiving anatomical regions of interest of multiple patients therein and having multiple apertures therethrough, each said aperture providing patient access to the imaging volume;
(b) multiple patient handling systems, each of said patient handling systems accessing said imaging volume through a respective one of said multiple apertures of said magnet, where at least two of said patient handling systems are in simultaneous use positioning anatomical regions of interest of at least two patients, respectively, within said imaging volume of said magnet; and
(c) a radio frequency antenna system for detecting magnetic resonance imaging data simultaneously from the anatomical regions of interest of said at least two patients within said imaging volume; and
(d) means for demarcating and separating said magnetic resonance imaging data for said at least two patients into separate images corresponding to said anatomical regions of interest for each said patient.

22. The medical magnetic resonance imaging system as described in claim 21, wherein two of said patient handling systems simultaneously position anatomical regions of interest of two of said patients within said imaging volume of said magnet.

23. The medical magnetic resonance imaging system as described in claim 21, wherein said radio frequency antenna system comprises a single radio frequency antenna that transmits and receives radio frequency energy.

24. The medical magnetic resonance imaging system as described in claim 21, wherein said patient handling systems comprise motorized patient bed structures.

25. The medical magnetic resonance imaging system as described in claim 24, further comprising automatic patient sequence control means for automatically sequencing the patient handling systems to move the respective patient into and out of the imaging volume.

26. The medical magnetic resonance imaging system as described in claim 24, wherein said motorized patient bed structures are remotely controlled.

27. The medical magnetic resonance imaging system as described in claim 21, wherein each of said multiple apertures of said magnet has an axis along which said patient accesses the common imaging volume and at least two of said axes intersect.

28. The medical magnetic resonance imaging system as described in claim 21, wherein said means for demarcating comprises at least one fiducial marker to separate said anatomical regions of interest of said patients.

29. The medical magnetic resonance imaging system of claim 21, wherein said imaging volume is non-electromagnetically partitioned.

30. The medical magnetic resonance imaging system as described in claim 21, wherein said imaging volume is dimensioned such that substantially less than each patient's entire body is received within the volume.

31. A method of conducting a magnetic resonance imaging procedure on successive patients using a magnetic resonance imaging apparatus with multiple apertures therethrough each providing access to an imaging volume for receiving anatomical regions of interest of said successive patients therein and with multiple patient handling systems that position said anatomical regions of interest of said successive patients within said imaging volume, comprising the following steps:
(a) loading a first patient onto a first movable bed structure of one of said patient handling systems;
(b) moving said first movable bed having said first patient thereon through one of said apertures into said imaging volume;
(c) positioning a first radio frequency antenna system relative to the anatomical region of interest of said first patient;
(d) performing a magnetic resonance scan protocol on said first patient;
(e) loading a second patient onto a second movable bed structure of a second of said patient handling systems while performing said magnetic resonance scan protocol on said first patient;
(f) removing said first patient from said imaging volume through said one of said apertures following completion of said magnetic resonance scan protocol on said first patient;
(g) moving said second movable bed having said second patient thereon into a second of said apertures;
(h) positioning a second radio frequency antenna relative to the anatomical region of interest of said second patient;
(i) performing a magnetic resonance scan protocol on said second patient; and
(j) removing said second patient from said imaging volume through said second of said apertures following completion of said magnetic resonance scan protocol on said second patient.

32. The method as described in claim 31, which includes unloading said first patient from the first movable bed structure and loading a third patient onto the first movable bed structure, during the performance of the magnetic resonance scan protocol on said second patient.

33. The method as described in claim 32, wherein said third patient is loaded onto a third movable bed structure of a third of said patient handling systems.

34. The method as described in claim 31, wherein step (c) is conducted prior to step (b) and step (h) is conducted prior to step (g).

35. The method of claim 31, wherein the first and second radio frequency antenna systems are the same, steps (b) and (c) are conducted simultaneously and steps (g) and (h) are conducted simultaneously such that as the anatomical regions of interest of said first and second patients are positioned in said imaging volume, the radio frequency antenna system is positioned relative to the anatomical regions of interest of each of said patients.

36. The method as described in claim 31, wherein said first and second apertures are adjacent to each other and said first and second movable beds are moved into said imaging volume along intersecting axes.

37. A method of conducting a magnetic resonance imaging procedure on patients using a magnetic resonance imaging apparatus with multiple apertures therethrough each providing access to an imaging volume for receiving anatomical regions of interest of multiple patients therein and with multiple patient handling systems, comprising the following steps;

(a) loading a first patient onto a first movable bed structure of one of said patient handling systems and a second patient onto a second movable bed structure of a second of said patient handling systems;

(b) simultaneously moving said first patient on said first movable bed and said second patient on said second movable bed through a first and a second of said multiple apertures, respectively, into said imaging volume;

(c.1) positioning a first radio frequency antenna system relative to the anatomical region of interest of said first patient;

(c.2) positioning a second radio frequency antenna system relative to the anatomical region of interest of said second patient; and (d) performing a magnetic resonance scan on said first patient and said second patient simultaneously.

38. The method as described in claim 37, wherein steps (c.1) and (c.2) are conducted prior to step (b).

39. The method as described in claim 37, wherein said positioning step further comprises positioning the anatomical regions of interest of said first and second patients adjacent to each other.

40. The method of claim 37, wherein said positioning step further comprises moving said first and second patients into said imaging volume along intersecting axes.

41. The method of claim 37, wherein the first and second radio frequency antenna systems are the same and steps (c.1) and (c.2) are conducted simultaneously with step (b) such that as the anatomical regions of interest of said first and second patients are positioned in said imaging volume, the radio frequency antenna system is positioned relative to the anatomical regions of interest of each of said patients.

42. The method as described in claim 37, wherein said first and second apertures are adjacent to each other and said first and second movable beds are moved into said imaging volume along intersecting axes.

43. A method of conducting a magnetic resonance imaging procedure on multiple patients using a magnetic resonance imaging apparatus with multiple apertures therethrough each providing access to an imaging volume for receiving anatomical regions of interest of said multiple patients therein and with multiple patient handling systems, comprising the following steps:

(a) loading a first patient onto a first movable bed structure of one of said patient handling systems, and a second patient onto a second movable bed structure of a second of said patient handling systems:

(b) simultaneously moving said first patient on said first movable bed and said second patient on said second movable bed through a first and a second of said multiple apertures, respectively, into said imaging volume;

(c.1) positioning a first radio frequency antenna system relative to the anatomical region of interest of said first patient;

(c.2) positioning a second radio frequency antenna system relative to the anatomical region of interest of said second patient;

(d) performing a magnetic resonance scan protocol on said first patient and said second patient simultaneously; and (e) demarcating and separating data obtained during said magnetic resonance scan protocol into separate images corresponding to said respective anatomical regions of interest of said first patient and said second patient.

44. The method as described in claim 43, wherein steps (c.1) and (c.2) are conducted prior to step (b).

45. The method as described in claim 43, wherein said positioning step further comprises positioning the anatomical regions of interest of said first and second patients adjacent to each other.

46. The method of claim 43, wherein said positioning step further comprises moving said first and second patients into said imaging volume along intersecting axes.

47. The method of claim 43, wherein the first and second radio frequency antenna systems are the same and steps (c.1) and (c.2) are conducted simultaneously with step (b) such that as the anatomical regions of interest of said first and second patients are positioned in said imaging volume, the radio frequency antenna system is positioned relative to the anatomical region of interest of each of said patients.

48. The method as described in claim 43, wherein said first and second apertures are adjacent to each other and said first and second movable beds are moved into said imaging volume along intersecting axes.

49. A method of conducting a magnetic resonance imaging procedure on successive patients using a magnetic resonance imaging apparatus with multiple apertures therethrough each providing access to an imaging volume for receiving anatomical regions of interest of said successive patients therein and with multiple patient handling systems that position said anatomical regions of interest of said successive patients within said imaging volume, comprising the following steps:

(a) loading a first patient onto a first movable bed structure of one of said patient handling systems;

(b) moving said first patient on said first movable bed into one of said apertures, into said imaging volume;

(c) positioning a first radio frequency antenna system relative to the anatomical region of interest of said first patient;

(d) performing a magnetic resonance scan protocol on said first patient;

(e) loading a second patient onto a second movable bed structure off a second of said patient handling systems while performing said magnetic resonance scan protocol on said first patient;

(f) removing said first patient from said imaging volume through said one of said apertures following completion of said magnetic resonance scan protocol on said first patient;

(g) moving said second patient on said second movable bed through a second of said apertures into said imaging volume;

(h) positioning a second radio frequency antenna system relative to the anatomical region of interest of said second patient;

(i) performing a magnetic resonance scan protocol on said second patient;

(j) removing said second patient from said imaging volume through said second of said apertures following completion of said magnetic resonance scan protocol on said second patient; and (k) automatically sequencing steps (f)–(g) for removing said first patient from said imaging volume and moving said second patient through said second of said apertures and into said imaging volume.

50. The method as described in claim 49, wherein said automatically sequencing step further comprises said step (i) for performing said scan protocol on said second patient.

51. A medical magnetic resonance imaging system comprising:
   (a) a magnet having an imaging volume for receiving anatomical regions of interest of multiple patients therein and having multiple apertures therethrough, each said aperture providing patient access to the imaging volume;
   (b) multiple patent handling systems, each of said patient handling systems accessing said imaging volume through a respective one of said multiple apertures of said magnet, each of said patent handling systems comprising a motorized patient bed structure for positioning a respective one off said anatomical regions of interest of one of said multiple patents within said imaging volume of said magnet;
   (c) automatic patient sequence control means for automatically sequencing said multiple patient handling systems to move the respective patients on said patient bed structure into and out off said imaging volume; and
   (d) a radio frequency antenna system for transmitting radio frequency energy into said imaging volume and detecting magnetic resonance imaging data from each of said anatomical regions of interest for each of said patients within said imaging volume of said magnet.

52. The medical magnetic resonance imaging system as described in claim 51, wherein said imaging volume comprises at least one fiducial marker to separate said anatomical regions of interest of said patients.

53. A medical magnetic resonance imaging system comprising:
   (a) a magnet having an imaging volume for receiving anatomical regions of interest of multiple patients therein and having multiple apertures therethrough, each said aperture providing patient access to the imaging volume;
   (b) multiple patient handling systems, each of said patient handling systems accessing said imaging volume through a respective one of said multiple apertures of said magnet, each of said patient handling systems comprising a motorized patient bed structure, where at least two of said motorized patient bed structures are in simultaneous use positioning anatomical regions of interest of at least two patients, respectively, thereon within said imaging volume of said magnet;
   (c) automatic patient sequence control means for automatically sequencing said multiple patient handling systems to move the respective patients on said bed structures into and out of said imaging volume; and
   (d) a radio frequency antenna system for detecting magnetic resonance imaging data simultaneously from the anatomical regions of interest of said at least two patients within said imaging volume.

54. A medical magnetic resonance imaging system comprising:
   (a) a magnet having an imaging volume for receiving anatomical regions of interest of multiple patients therein and having multiple apertures therethrough, each said aperture providing patient access to the imaging volume;
   (b) multiple patient handling systems, each of said patient handling systems accessing said imaging volume through a respective one of said multiple apertures of said magnet, each of said patient handling systems comprising a motorized patient bed structure, where at least two of said motorized patient bed structures are in simultaneous use positioning anatomical regions of interest of at least two patients, respectively, therein within said imaging volume of said magnet;
   (c) automatic patient sequence control means for automatically sequencing said multiple patient handling systems to move the respective patients on said bed structures into and out of said imaging volume;
   (d) a radio frequency antenna system for detecting magnetic resonance imaging data simultaneously from the anatomical regions of interest of said at least two patients within said imaging volume; and
   (e) means for demarcating and separating said magnetic resonance imaging data for said at least two patients into separate images corresponding to said anatomical regions of interest for each said patient.

55. A medical magnetic resonance imaging system comprising:
   (a) a magnet having an imaging volume for receiving anatomical regions of interest of multiple patients therein and having multiple apertures therethrough, each said aperture providing patient access to the imaging volume;
   (b) multiple patient handling systems, each of said patient handling systems accessing said imaging volume through a respective one of said multiple apertures of said magnet, where at least two of said patient handling systems are in simultaneous use positioning anatomical regions of interest of at least two patients, respectively, within said imaging volume of said magnet; and
   (c) a single radio frequency antenna that transmits radio frequency energy into said imaging volume and receives radio frequency energy from the anatomical regions of each of said patients.

* * * * *

UNITED STATES PATENT AND TRADEMARK OFFICE
CERTIFICATE OF CORRECTION

PATENT NO.   : 5,606,970
DATED        : March 4, 1997
INVENTOR(S)  : Raymond V. Damadian It is certified that error appears in the above-identified patent and that said Letters Patent is hereby corrected as shown below:

Col. 1, line 54, "described" should read --describe --.
Col. 8, line 21, "ad" should read --as--.
Col. 12, line 23, "region" should read --regions--.
Col. 12, line 48, "off" should read --of--.
Col. 13, line 15, "patent" should read --patient--.
Col. 13, line 18, "patent" should read --patient--.
Col. 13, line 20, "off" should read --of--.
Col. 13, line 21, "patents" should read --patients--.
Col. 13, line 27, "off" should read --of--.

Signed and Sealed this

Sixteenth Day of June, 1998

Attest:

BRUCE LEHMAN

Attesting Officer

Commissioner of Patents and Trademarks